United States Patent
Suck et al.

(10) Patent No.: US 8,048,424 B2
(45) Date of Patent: Nov. 1, 2011

(54) INSECT POISON ALLERGENS WITH REDUCED IGE REACTIVITY AND METHOD FOR PRODUCING THE SAME

(75) Inventors: Roland Suck, Hamburg (DE); Oliver Cromwell, Wentorf (DE); Helmut Fiebig, Schwarzenbek (DE)

(73) Assignee: Merck Patent GmbH, Darmstadt (DE)

( * ) Notice: Subject to any disclaimer, the term of this patent is extended or adjusted under 35 U.S.C. 154(b) by 46 days.

(21) Appl. No.: 11/889,108

(22) Filed: Aug. 9, 2007

(65) Prior Publication Data

US 2007/0280884 A1 Dec. 6, 2007

Related U.S. Application Data

(62) Division of application No. 10/148,565, filed as application No. PCT/EP00/11776 on Nov. 27, 2000, now Pat. No. 7,285,397.

(30) Foreign Application Priority Data

Dec. 1, 1999 (DE) .................................. 199 57 904

(51) Int. Cl.
- A61K 38/00 (2006.01)
- A61K 39/00 (2006.01)
- A61K 39/35 (2006.01)
- A61K 39/36 (2006.01)
- A01N 37/18 (2006.01)
- C07K 1/00 (2006.01)
- C07K 14/00 (2006.01)
- C07K 17/00 (2006.01)

(52) U.S. Cl. .................... 424/185.1; 424/275.1; 514/1.1; 530/350

(58) Field of Classification Search .......................... None
See application file for complete search history.

(56) References Cited

U.S. PATENT DOCUMENTS 5,804,201 A * 9/1998 King .......................... 424/275.1

OTHER PUBLICATIONS

Larche et al. 'Immunological mechanisms of allergen-specific immunotherapy.' Nat. Rev. Immunol. 6(10):761-771, 2006.*
Mukhopadhyay et al. 'Inclusion bodies and purification of proteins in biologically active forms.' Adv. Biochem. Eng. 56:61-109, 1997.*
Howlett et al. 'Role of carbohydrates as an antigenic determinant of a glycoprotein from rye-grass (*Lolium perenne*) pollen.' Biochem. J. 197:707-714, 1981.*
King, et al., "Murine T and B Cell Response to Natural and Recombinant Hornet Venom Allergen Do1 m 5.02 and its Recombinant Fragments", The Journal of Immunology, vol. 154, pp. 577-584, 1995.
Suck, et al., "Purification and Immunobiological Characterization of Folding Variants of the recombinant Major Wasp Allergen ves v 5 (Antigen 5)", International Archives of Allergy and Immunology, vol. 121, pp. 284-291, Apr. 2000.
Monsalve, et al., "Expressions of Recombinant Venom Allergen, Antigen 5 of Yellowjacket (*Vespula vulgaris*) and Paper Wasp (*Polistes annularis*), in Bacteria and Yeast", Protein Expression and Purification, vol. 16, pp. 410-416, Aug. 1999.
Forster et al., "Natural and Recombinant Enzymatically Active or Inactive bee venom Phospholipase A2 has the same Potency to Release Histamine from Basophils in Patients with Hymenoptera Allergy", The Journal of Allergy and Clinical Immunology, vol. 95, pp. 1229-1235, 1995.
Soldatova, et al., "Superior Biologic Activity of the Recombinant bee venom Allergen Hyaluronidase Expressed in Baculovirus-Infected Insect Cells as Compared with *Escherichia coli*", The Journal of Allergy and Clinical Immunology, vol. 101, pp. 691-698, 1998.
Fang et al., "cDNA cloning and primary structure of a white-face hornet venom allergen, antigen 5", Proc. Natl. Acad. Sci. USA, vol. 85, pp. 895-899, Feb. 1988.
King et al., "Hymenoptera Allergens, in Allergens and Allergen Immunotherapy", third edition, Macel Dekker, Inc. 2004, pp. 339-353.
Rudolph et al., Faseb J, 1996, 10:49-56.
Cabrita et al., Biotechnol Annu Rev. 2004, 10:31-50.
Fischer, BE Bitech Adv, 1994, 12:89-101.

* cited by examiner

*Primary Examiner* — Nora Rooney
(74) *Attorney, Agent, or Firm* — Millen, White, Zelano, Branigan, P.C.

(57) ABSTRACT

The invention relates to recombinant insect poison allergens and to a specific method for producing them. Said allergens can be varied according to whether they are produced using folds (conformations) that are identical or different to those that occur naturally. The proteins with folds that do not occur naturally have a reduced IgE reactivity or allergenity and can therefore be used as therapeutic agents in the immunotherapy of allergies.

7 Claims, No Drawings

INSECT POISON ALLERGENS WITH REDUCED IGE REACTIVITY AND METHOD FOR PRODUCING THE SAME

This application is a divisional application of U.S. Ser. No. 10/148,565, filed on Sep. 4, 2002 now U.S. Pat. No. 7,285,397; U.S. Ser. No. 10/148,565 is a §371 National Stage application of International Application No. PCT/EP00/11776 filed Nov. 27, 2000.

The invention relates to recombinant insect poison allergens and to a method for targeted production thereof, where the said allergens can be differentiated by nature-identical or nature-contrary folds (conformations), depending on the performance of the production method.

An application of fold shapes which correspond to the natural molecule consists in single-allergen-differentiated diagnostics (in vitro or in vivo) of allergy sufferers, specifically insect poison allergy sufferers.

The nature-contrary fold shapes can be employed as therapeutic agents for specific immunotherapy which have low side effects. These recombinant fold variants could thus effect safer treatment than the natural product. The method is designed in such a way that biotechnological production can be carried out under conditions which are necessary for pharmaceuticals (GMP).

Insect sting allergies are caused principally by wasps and honey bees and can result in severe systemic symptoms or even potentially fatal anaphylaxia (Müller, U. R., in: Insect sting allergy, Gustav Fischer Verlag; 1990). The substances which trigger type 1 allergy are proteins, glycoproteins or polypeptides of the insect venom. These allergens react, after injection, with the IgE molecules bound to the surface of mast cells in sensitised persons. If FcεRI-bound IgE molecules of this type are crosslinked to one another by an allergen, this results in the release of mediators (for example histamine, leukotrienes) and cytokines by the effector cell and thus in the corresponding clinical symptoms.

Besides the peptide melittin, the enzymes hyaluronidase and phospholipase A2 act as allergenic constituents of bee venom (Habermann, E., 1972, Science 177, 314-322). In the case of the wasp, the main enzymatically active allergens are likewise a hyaluronidase, which is similar to that of bee venom (Hoffmann, D. R., 1986, J. Allergy Clin. Immunol. 78, 337-343), and a phospholipase A1. The most important main allergen of wasp poison is antigen 5, for which no enzymatic activity has hitherto been detected (King et al., 1978, Biochemistry 17, 5165-5174). All of the said allergens have already been characterized in molecular biological terms and the corresponding cDNA molecules have been cloned (inter alia Fang et al., 1988, PNAS, 895-899; Soldatova et al., 1993, FEBS, 145-149; Kuchler et al., 1989, Eur. J. Biochem. 184, 249-254). With the aid of cDNA sequences, it is possible to produce recombinant allergens which could be used in diagnostics and therapy of allergies (Scheiner and Kraft, 1995, Allergy 50, 384-391).

In connection with the present invention, the main allergen antigen 5 is of particular importance since the invention uses this molecule by way of example. It is a non-glycosylated protein with a size of about 25 kDa. The primary sequence contains 8 cysteine residues, which indicates four disulfide bridges (Hoffman, D. R., 1993, J. Allergy Clin Immunol. 92: 707-716).

A classical approach to effective therapeutic treatment of insect poison allergies is specific immunotherapy or hyposensitisation (Müller, U. R., in: Insect sting allergy, Gustav Fischer Verlag; 1990). Here, natural allergen extracts are injected subcutaneously into the patient in increasing doses. However, this method entails the risk of allergic reactions or even anaphylactic shock. Since strong reactions can be expected especially in the case of insect sting hyposensitisation, treatment is currently exclusively carried out as an in-patient.

Therapy optimization with allergens produced by recombinant methods would be particularly possible in the case of insect sting allergy. Defined cocktails, optionally matched to individual sensitisation patterns of the patients, of high-purity allergens produced by recombinant methods (Scheiner and Kraft, 1995) could replace extracts from natural allergen sources. Realistic perspectives which may result in safer hyposensitisation with recombinant allergens of this type are offered by deliberately mutated recombinant allergens in which IgE epitopes are specifically deleted without impairing the T-cell epitopes which are essential for the therapy (Schramm et al., 1999, J. Immunol. 162, 2406-2414).

It is known from heterologous expression in *E. coli* that most eukaryontic proteins do not adopt the 'natural' conformation or only do so to a small extent. A consequence of these incorrect folds is frequently insolubility of these proteins. This is observed in particular in cysteine-containing proteins (Kuchler et al., 1989, Eur. J. Biochem. 184, 249-254). It has been reported of antigen 5 in particular that expression in bacteria results in insoluble aggregates which do not have the natural conformation (Monsalve et al., 1999, Protein Express Purif. 16(3): 410-416). Insoluble aggregates of this type cannot be used either for diagnostics or for therapy.

The proteins which are insoluble in *E. coli* are frequently prepared for research purposes in a eukaryontic expression system, such as, for example, yeast or insect cells (Monsalve et al., 1999, Protein Express Purif 16(3): 410-416; Soldatova et al., 1998, J Allergy Clin Immunol 101: 691-698). However, disadvantages of eukaryontic expression systems are in particular possible hyperglycosylations (Grobe et al., 1999, Eur J Biochem 263: 33-40), proteolytic degradation processes and comparatively small product yields (Glover and Hames (eds.), 1995, Expression Systems, IRL Press, Oxford-New York-Tokyo). Proteins of this type are therefore usually unsuitable for allergological use in the sense of pharmaceutical-medical diagnostics and therapy.

The products of the method according to the invention which have the natural conformation can advantageously be used in in-vitro and in-vivo diagnostics of allergic disorders, especially insect sting allergy. This nature-identical fold shape is available for the detection of IgE antibodies in established methods.

On the other hand, the variants produced with the aid of the invention which are distinguished by an essentially non- or only partially IgE-reactive conformations can be used as hypoallergenic components in preparations for specific immunotherapy. The term "hypoallergenic" above and below is taken to mean, in accordance with the invention, reduced to absent, preferably from 5 to 95%, in particular from 20 to 85%, reduced allergeneity (compared with the natural allergen) due to a reduced IgE response.

The present invention is a method with which recombinant allergens can be produced in bacteria (*E. coli*). A first purification step takes place through considerable enrichment of the insoluble protein aggregates, These aggregates are then denatured without addition of reducing agents. Depending on the subsequent dialysis conditions, different fold shapes are obtained. It is crucial that these molecules are monomeric and soluble. The first soluble fold variant has an IgE reactivity which is comparable with that of the natural allergen and can accordingly be used for diagnostic purposes. A product of this type is obtained by dialysis with cysteine-containing solution.

The other alternative soluble fold variants are structurally different from the natural allergen and are distinguished by reduced or absent IgE reactivity. For this reason, variants of this type are suitable for facilitating improved immunotherapy. A hypoallergenic product of this type is obtained in accordance with the invention by dialysis with acidic buffers, preferably in a pH range between 3.5 and 6.5, in particular between 4.0 and 5.5.

The invention thus relates to recombinant insect allergen which is characterized in that it has reduced IgE reactivity or allergeneity. In accordance with the invention, the allergeneity of these proteins is reduced by up to 95% compared with the natural allergen.

In particular, the invention relates to a corresponding recombinant wasp insect allergen, in particular from *Vespula vulgaris* and *Vespula germanica*.

The invention furthermore relates to a method for isolating essentially pure recombinant insect poison allergens which is characterized in that the allergenic proteins are produced in insoluble form as "inclusion bodies" in bacteria cells, the said insoluble aggregates are denatured, and the denatured products are converted by dialysis into soluble, monomeric allergens of different fold conformations and isolated. The said denaturing is preferably carried out using guanidinium chloride without addition of reducing agents.

The invention relates, in particular, to a method for isolating recombinant insect poison allergens with reduced allergeneity, or IgE reactivity, in which the dialysis is carried out using acidic buffer, preferably sodium acetate buffers having a pH of between 4.5 and 5.0.

However, the invention also relates to a method for isolating recombinant insect poison allergens with normal allergeneity, or IgE reactivity, in which the dialysis is carried out using cysteine-containing solutions.

The invention also relates to a recombinant wasp poison allergen which is obtainable by the corresponding method described above and below.

The invention furthermore relates to a pharmaceutical preparation which comprises a corresponding recombinant allergen with reduced or diminished IgE reactivity and corresponding adjuvants and excipients.

Finally, the invention relates to the use of insect poison allergens obtainable by a corresponding method described above or below for the in-vivo and in-vitro diagnosis of insect sting allergies.

The method is described in detail below:

By way of example, the wasp poison allergens antigen 5 from *Vespula vulgaris* (Ves v 5) and antigen 5 from *Vespula germanica* (Ves g 5) were cloned into the expression vector pSE420 and transformed into the K12 bacteria strain M15 pREP4. A flow chart for this method is shown in Figure 1.

The recombinant allergens are produced using a preculture of the strain for inoculation of an expression culture. The expression, induced by IPTG, is carried out in a chicane flask at 37° C. in LB medium with limited oxygen supply (90 rpm/min). The bacteria are harvested by centrifugation (5000×g, 10 min, 20° C.) after expression for 5 hours. The bacterial digestion is carried out after resuspension of the cells in buffer (50 mM tris/HCl, 25% (w/v) sucrose, pH 8.0) by lysozyme addition (10 µg/g wet weight). This is followed by addition of the same volume of detergent solution (0.2 M NaCl, 1% (w/v) DOC, 1% (w/v) Nonidet P40). This digestion solution is subsequently treated with ultrasound (3 min on ice, 130 watts, 0.5 s pulse). Since the expression products are primarily in the form of insoluble aggregates (inclusion bodies), they can be separated from the majority of the remaining components (cell wall fragments, ribosomes, etc.) by centrifugation at 3000×g owing to their high density. The further purification is carried out by three successive washing steps with detergent-containing solutions (1% Triton X-100). The purified inclusion bodies are subsequently digested by addition of denaturing buffer (6M guanidinium chloride, 20 mM tris/HCl, pH 8.0) and shaken for 2 hours at RT.

In order to isolate IgE-reactive fold shapes, the denaturing batch is introduced into a dialysis tube (digestion limit 12-14 kDa) and dialysed against 100 times the volume of cysteine solution (5 mM cysteine) for 12 hours at RT with stirring. This is followed by dialysis against distilled water in order to remove the cysteine.

In order to obtain conformations with reduced IgE reactivity, the first dialysis will be carried out against 20 mM sodium acetate buffer (pH 5.0). Here too, further dialysis against distilled water is carried out. After removal, the water-soluble allergens are separated off from the precipitated aggregates by centrifugation. The supernatant contains the desired soluble recombinant allergens. Instead of sodium acetate buffer, it is also possible to use other acidic buffers which are capable of buffering in a range from 3.5 to 6.5, preferably from 4.0 to 5.5. Examples of buffer systems of this type are adequately described in the literature.

The precipitated recombinant allergens produced in both methods can be re-denatured and treated in accordance with the same scheme. This significantly increases the yield.

After the dialysis steps, the products have a purity of about 95%. Further purification steps of the basic insect poison allergens are cation exchange chromatography (buffer pH 7.2) with, for example, Source S (Pharmacia, Freiburg, Germany) and gel filtration. In addition to the removal of high- and low-molecular-weight minimal impurities, gel filtration also serves for desalination.

Quality control of the products is based on the following characteristic properties, which are summarised in tabular form for antigen 5:

| Property | Fold with natural IgE reactivity | Fold with reduced IgE reactivity |
| --- | --- | --- |
| Apparatus. MW in the SDS-page (non-reducing cond.) | 25 kDa | 26-27 kDa |
| Salt conc. for elution in Source S | 320 mM NaCl | 400 mM NaCl |
| Cleavage with protease V8 | 15 kDa fragment + peptides | peptides <10 kDa |
| Antigen 5 specific monoclonal antibodies | detection by 8E3, 1E11 | detection only possible with 8E3 |
| Frequency IgE reactivity with sera from allergy sufferers | >95% | <10% |
| Allergenic power | similar to n-antigen 5 | >10 × less than nAg5 | n-antigen = natural antigen

The method according to the invention is suitable for all types of insect poison allergens. The purification techniques used and recombinant cloning and expression techniques are known and available to the person skilled in the art and can be replaced by known similar methods.

We claim:

1. A *Vespula* wasp poison allergen antigen 5 of *Vespula vulgaris* or *Vespula germanica* having reduced IgE reactivity and which is produced recombinantly in bacteria, wherein said *Vespula* wasp poison allergen antigen is non-glycosylated monomeric, full-length and soluble in distilled water and is obtained by expressing said *Vespula* wasp poison allergen antigen 5 in bacteria in an insoluble form as inclusion bodies, denaturing said inclusion bodies using guanidinium chloride without addition of any reducing agent, dialyzing said denatured product against an acidic buffer wherein said acidic buffer does not comprise any reducing agent, and performing a final dialysis against distilled water.

2. A non-glycosylated, monomeric, full-length and water-soluble recombinant *Vespula* wasp poison allergen antigen 5 according to claim 1, wherein said dialysis against an acidic buffer is performed with an acidic buffer having a pH of between 3.5 and 6.5.

3. A non-glycosylated, monomeric, full-length and water-soluble recombinant *Vespula* wasp poison allergen antigen 5 according to claim 1, wherein said dialysis against an acidic buffer is performed with an acidic buffer having a pH of between 4.5 and 5.0.

4. A non-glycosylated, monomeric, full-length and water-soluble recombinant *Vespula* wasp poison allergen antigen 5 according to claim 1, wherein said dialysis against an acidic buffer is performed with sodium acetate buffer having a pH of between 4.5 and 5.0.

5. The non-glycosylated, monomeric, full-length and water-soluble recombinant *Vespula* wasp poison allergen antigen 5 according to claim 1 comprising a molecular weight of 25-27 kDa as measured using sodium dodecyl sulfate polyacrylamide gel electrophoresis (SDS-PAGE) under non-reducing conditions.

6. The non-glycosylated, monomeric, full-length and water-soluble recombinant *Vespula* wasp poison allergen antigen 5 according to claim 5 comprising eight cysteine residues.

7. A pharmaceutical composition which comprises a non-glycosylated monomeric, full-length and water-soluble recombinant *Vespula* wasp poison allergen antigen 5 according to claim 1 and an adjuvant or excipient.

* * * * *